US006982316B1

(12) United States Patent
Scanlan et al.

(10) Patent No.: US 6,982,316 B1
(45) Date of Patent: Jan. 3, 2006

(54) ISOLATED NUCLEIC ACID MOLECULES ASSOCIATED WITH COLON CANCER AND METHODS FOR DIAGNOSING AND TREATING COLON CANCER

(75) Inventors: Matthew J. Scanlan, New York, NY (US); Yao-Tseng Chen, New York, NY (US); Elisabeth Stockert, New York, NY (US); Lloyd J. Old, New York, NY (US)

(73) Assignees: Ludwig Institute for Cancer Research, New York, NY (US); The New York Hospital-Cornell Medical Center, New York, NY (US)

( * ) Notice: Subject to any disclaimer, the term of this patent is extended or adjusted under 35 U.S.C. 154(b) by 0 days.

(21) Appl. No.: 09/502,945

(22) Filed: Feb. 11, 2000

Related U.S. Application Data

(62) Division of application No. 08/948,705, filed on Oct. 10, 1997, now Pat. No. 6,043,084.

(51) Int. Cl.
*C07K 14/47* (2006.01)
*C07K 7/00* (2006.01)

(52) U.S. Cl. .................... 530/350; 530/300; 424/184.1

(58) Field of Classification Search ............. 424/277.1, 424/184.1; 530/350, 300
See application file for complete search history.

(56) References Cited

U.S. PATENT DOCUMENTS

| | | | | |
|---|---|---|---|---|
| 5,470,730 A | * | 11/1995 | Greenberg et al. | |
| 5,698,396 A | | 12/1997 | Pfreundschuh | |
| 5,840,839 A | * | 11/1998 | Wang et al. | 530/325 |
| 6,025,191 A | | 2/2000 | Pfreundschuh | |

OTHER PUBLICATIONS

Sahin et al., Proc. Natl. Acad. Sci., vol. 92, pp. 11810-11813, Dec. 1995.*
Alberts, et al. (Molecular Biology of the Cell, 3rd edition, 1994.*
Scalan et al (1998, Int. J. Cancer, vol. 76, pp. 652-658.*
Riott et al (Immunology, Fourth Edition, 1996, Mosby, p. 7.9-7.11.*
Peltz et al p. 1729 (1999, J. Exp. Med. vol. 190, pp. 1729-1731).*
de Plaen et al., *Proc. Natl. Sci. USA* 85:2275, 1988.
Mandelboim et al., *Nature* 369:69 1994.
van der Bruggen et al., *Science* 254:1643-1647, 1991.
Brichard et al., *J. Exp. Med.* 178:489-495, 1993.
Coulie et al., *J. Exp. Med.* 180:35-42, 1994.
Kawakami et al., *Proc. Natl. Acad. Sci. USA* 91:3515-3519, 1994.
Oettgen et al., *Immunol. Allerg. Clin. North. Am.* 10:607-637, 1990.
Sahin et al., *Proc. Natl. Acad. Sci. USA* 92:11810-11913, 1995.
Crew et al., *EMBO J* 144:2333-2340, 1995.
Chen et al., *Proc. Natl. Acad. Sci. USA* 94: 1914-1918 (1997).

* cited by examiner

*Primary Examiner*—Jeffrey Siew
*Assistant Examiner*—Misook Yu
(74) *Attorney, Agent, or Firm*—Wolf, Greenfield & Sacks P.C.

(57) ABSTRACT

Various molecules associated with disorders such as cancer are disclosed. The invention also discloses diagnostic aid therapeutic methods based upon these molecules, as well as compositions for stimulating an immune response and methods for identifying cancer-associated nucleic acid and polypeptide molecules.

14 Claims, No Drawings

SEQUENCE LISTING

```
<160> NUMBER OF SEQ ID NOS: 8

<210> SEQ ID NO 1
<211> LENGTH: 1552
<212> TYPE: DNA
<213> ORGANISM: Homo Sapiens

<400> SEQUENCE: 1

cttctggatg catccgagaa gctaaaactt acttatgagg aaaagtgtga aattgaggaa     60

tcccaattga agtttttgag gaacgactta gctgaatatc agagaacttg tgaagatctt    120

aaagagcaac taaagcataa agaatttctt ctggctgcta atacttgtaa ccgtgttggt    180

ggtctttgtt tgaaatgtgc tcagcatgaa gctgttcttt cccaaaccca tactaatgtt    240

catatgcaga ccatcgaaag actggttaaa gaaagagatg acttgatgtc tgcactagtt    300

tccgtaagga gcagcttggc agatacgcag caaagagaag caagtgctta tgaacaggtg    360

aaacaagttt tgcaaatatc tgaggaagcc aattttgaaa aaaccaaggc tttaatccag    420

tgtgaccagt tgaggaagga gctggagagg caggcggagc gacttgaaaa agaacttgca    480

tctcagcaag agaaaagggc cattgagaaa gacatgatga aaaaggaaat aacgaaagaa    540

agggagtaca tgggatcaaa gatgttgatc ttgtctcaga atattgccca actggaggcc    600

caggtggaaa aggttacaaa ggaaaagatt tcagctatta atcaactgga ggaaattcaa    660

agccagctgg cttctcggga aatggatgtc acaaaggtgt gtggagaaat gcgctatcag    720

ctgaataaaa ccaacatgga gaaggatgag gcagaaaagg agcacagaga gttcagagca    780

aaaactaaca gggatcttga aattaaagat caggaaatag agaaattgag aatagaactg    840

gatgaaagca aacaacactt ggaacaggag cagcagaagg cagccctggc cagagaggag    900
```

-continued

```
tgcctgagac taacagaact gctgggcgaa tctgagcacc aactgcacct caccagatct    960

gaaatagctc aactcagtca agaaaaaagg tatacatatg ataaattggg aaagttacag   1020

agaagaaatg aagaattgga ggaacagtgt gtccagcatg ggagagtaca tgagacgatg   1080

aagcaaaggc taaggcagct ggataagcac agccaggcca cagcccagca gctggtgcag   1140

ctcctcagca agcagaacca gcttctcctg gagaggcaga gcctgtcgga agaggtggac   1200

cggctgcgga cccagttacc cagcatgcca caatctgatt gctgacctgg atggaacaga   1260

gtgaaataaa tgaattacaa agagatattt acattcatct ggtttagact taatatgcca   1320

caacgcacca cgaccttccc agggtgacac cgcctcagcc tgcagtgggg ctggtcctca   1380

tcaacgcggg cgctgtcccc gcacgcagtc gggctggagc tggagtctga ctctagctga   1440

gcagactcct ggtgtatgtt ttcagaaatg gcttgaagtt atgtgtttaa atctgctcat   1500

tcgtatgcta ggttatacat atgattttca ataaatgaac tttttaaaga aa           1552
```

<210> SEQ ID NO 2
<211> LENGTH: 2885
<212> TYPE: DNA
<213> ORGANISM: Homo Sapiens

<400> SEQUENCE: 2

```
ggaattcctc ttgtcgaagt caaaggagcc cacaccaggc ggcctcaacc attccctccc     60

acagcacccc aaatgctggg gagcccacca tgcttctttg gaccagagtt cccctcccca    120

gagcggcccc cctgggacgc ctccctccta caaactgcct ttgcctgggc cctacgacag    180

tcgagacgac ttccccctcc gcaaaacagc ctctgaaccc aacttgaaag tgcgttcaag    240

gctaaaacag aaggtggctg agcggagaag cagtcccctc ctgcgtcgca aggatgggac    300

tgttattagc acctttaaga agagagctgt tgagatcaca ggtgccgggc ctggggcgtc    360

gtccgtgtgt aacagcgcac ccggctccgg ccccagctct cccaacagct cccacagcac    420

catcgctgag aatggcttta ctggctcagt ccccaacatc cccactgaga tgctccctca    480

gcaccgagcc ctccctctgg acagctcccc caaccagttc agcctctaca cgtctccttc    540

tctgcccaac atctccctag ggctgcaggc cacggtcact gtcaccaact cacacctcac    600

tgcctccccg aagctgtcga cacagcagga ggccgagagg caggccctcc agtccctgcg    660

gcagggtggc acgctgaccg gcaagttcat gagcacatcc tctattcctg gctgcctgct    720

gggcgtggca ctggagggcg acgggagccc ccacgggcat gcctccctgc tgcagcatgt    780

gctgttgctg gagcaggccc ggcagcagag caccctcatt gctgtgccac tccacgggca    840

gtccccacta gtgacgggtg aacgtgtggc caccagcatg cggacggtag gcaagctccc    900

gcggcatcgg cccctgagcc gcactcagtc ctcaccgctg ccgcagagtc cccaggccct    960

gcagcagctg gtcatgcaac aacagcacca gcagttcctg gagaagcaga agcagcagca   1020

gctacagctg ggcaagatcc tcaccaagac aggggagctg cccaggcagc ccaccaccca   1080

ccctgaggag acagaggagg agctgacgga gcagcaggag gtcttgctgg gggagggagc   1140

cctgaccatg ccccgggagg gctccacaga gagtgagagc acacaggaag acctggagga   1200

ggaggacgag gaagaggatg gggaggagga ggaggattgc atccaggtta aggacgagga   1260

gggcgagagt ggtgctgagg aggggcccga cttggaggag cctggtgctg gatacaaaaa   1320

actgttctca gatgcccaac cgctgcaacc tttgcaggtg taccaagcgc ccctcagcct   1380

ggccactgtg ccccaccaag ccctgggccg tacccaatcc tcccctgctg cccctggggg   1440

catgaagaac cccccagacc aacccgtcaa gcacctcttc accacaagtg tggtctacga   1500
```

-continued

```
cacgttcatg ctaaagcacc agtgcatgtg cgggaacaca cacgtgcacc ctgagcatgc   1560

tggccggatc cagagcatct ggtcccggct gcaggagaca ggcctgctta gcaagtgcga   1620

gcggatccga ggtcgcaaag ccacgctaga tgagatccag acagtgcact ctgaatacca   1680

caccctgctc tatgggacca gtcccctcaa ccggcagaag ctagacagca agaagttgct   1740

cggtcccatc agccagaaga tgtatgctgt gctgccttgt gggggcatcg ggtggacag   1800

tgacaccgtg tggaatgaga tgcactcctc cagtgctgtg cgcatggcag tgggctgcct   1860

gctggagctg gccttcaagg tggctgcagg agagctcaag aatggatttg ccatcatccg   1920

gcccccagga caccacgccg aggaatccac agccatggga ttctgcttct tcaactctgt   1980

agccatcacc gcaaaactcc tacagcagaa gttgaacgtg ggcaaggtcc tcatcgtgga   2040

ctgggacatt caccatggca atggcaccca gcaggcgttc tacaatgacc cctctgtgct   2100

ctacatctct ctgcatcgct atgacaacgg gaacttcttt ccaggctctg gggctcctga   2160

agaggttggt ggaggaccag gcgtggggta caatgtgaac gtggcatgga caggaggtgt   2220

ggaccccccc attggagacg tggagtacct tacagccttc aggacagtgg tgatgcccat   2280

tgcccacgag ttctcacctg atgtggtcct agtctccgcc gggtttgatg ctgttgaagg   2340

acatctgtct cctctgggtg gctactctgt caccgccaga tgttttggcc acttgaccag   2400

gcagctgatg accctggcag gggccgggt ggtgctggcc ctggagggag gccatgactt   2460

gaccgccatc tgtgatgcct ctgaagcttg tgtctcggct ctgctcagtg taaagctgca   2520

gcccttggat gaggcagtct tgcagcaaaa gcccaacatc aacgcagtgg ccacgctaga   2580

gaaagtcatc gagatccaga gcaaacactg gagctgtgtg cagaagttcg ccgctggtct   2640

gggccggtcc ctgcgagggg cccaagcagg tgagaccgaa gaagccgaaa tgtgaacgcc   2700

atggccttgc tgttggtggg ggccgaacag gcccaagctg cggcagcccg ggaacacagc   2760

cccaggccgg cagaggagcc catggagcag gagcctgccc tgtgacgccc cggcccccat   2820

ccctttgggc ttcaccattg tgattttgtt tattttttct attaaaaaca aaaagttaaa   2880

aattt                                                               2885
```

<210> SEQ ID NO 3
<211> LENGTH: 1298
<212> TYPE: DNA
<213> ORGANISM: Homo Sapiens
<220> FEATURE:
<221> NAME/KEY: unsure
<222> LOCATION: 55..55
<223> OTHER INFORMATION:
<220> FEATURE:
<221> NAME/KEY: unsure
<222> LOCATION: 141..141
<223> OTHER INFORMATION:
<220> FEATURE:
<221> NAME/KEY: unsure
<222> LOCATION: 199..99
<223> OTHER INFORMATION:
<220> FEATURE:
<221> NAME/KEY: unsure
<222> LOCATION: 342..342
<223> OTHER INFORMATION:
<220> FEATURE:
<221> NAME/KEY: unsure
<222> LOCATION: 352..352
<223> OTHER INFORMATION:
<220> FEATURE:
<221> NAME/KEY: unsure
<222> LOCATION: 722..722
<223> OTHER INFORMATION:
<220> FEATURE:

-continued

```
<221> NAME/KEY: unsure
<222> LOCATION: 750..750
<223> OTHER INFORMATION:
<220> FEATURE:
<221> NAME/KEY: unsure
<222> LOCATION: 1058..1058
<223> OTHER INFORMATION:
<220> FEATURE:
<221> NAME/KEY: unsure
<222> LOCATION: 1101..1101
<223> OTHER INFORMATION:
<220> FEATURE:
<221> NAME/KEY: unsure
<222> LOCATION: 1144..1144
<223> OTHER INFORMATION:

<400> SEQUENCE: 3

ggctgctgaa atgactgcga accggcttgc agagagcctt ctggctttga gccancagga     60

agaactagcg gatttgccaa aagactacct cttgagtgag agtgaagatg agggggacaa    120

tgatggagag agaaagcatc naaagcttct ggaagcaatc agttcccttg atggaaagaa    180

taggcggaaa ttggctgana ggtctgaggc tagtctgaag gtgtcagagt tcaatgtcag    240

ttctgaagga tcaggagaaa agctggtcct tgcagatctg cttgagcctg ttaaaacttc    300

atcttctttg gccactgtga aaaagcaact gagtagagtc anatcaaaga anacagtgga    360

gttacctctg aacaaagaag agattgaacg gatccacaga gaatagcatt caataaaacg    420

cacaagtcct ctccaaatgg gaccctgtcg tcctgaagaa ccggcaggca gagcagctgg    480

tttttcccct ggagaaagag gagccagcca ttgctcccat tgaacatgtg ctcagtggct    540

ggaaggcaag aactcccctg gagcaggaaa ttttcaacct cctccataag aacaagcagc    600

cagtgacaga ccctttactg acccctgtgg aaaaggcctc tctccgagcc atgagcctag    660

aagaggcaaa gatgcgacga gcagagcttc agagggctcg ggctctgcag tcctactatg    720

angccaaggc tcgaagagag aagaaaatcn aaagttaaaa gtatcacaaa gtcgtgaaga    780

aaggaaaggc caagaaagcc ctaaaagagt ttgagcagct gcggaaggtt aatccagctg    840

ccgcactaga agaacgaaga aaagaggaaa gaaggaggag gagaaagaag aagaacaagg    900

agaagaagaa agaagaaggg agaaggagaa gaaaagaagg agaagaggaa aaggaagaag    960

gagaaagaaa aggagaagga aaaggaaaag aaggagaaga aagaagaact aagaagaagg   1020

agaggaagaa taagaaggaa agaagaaaga aaaaagtnaa agaagaagaa agaaggaaga   1080

aggaaagaag aggaagaact nagaagaaga aagaggagga aagaagaaag aagaataagg   1140

aacnagaaag aaggagaaga aagaataaga agaggaagaa gaaaaagaag aaaagaagaa   1200

ggaaagaagg agaaaaagga agaaaaaagg aagaagaaag tagaaagcgg aagaaagaaa   1260

agaaagtata agaaggaaga agaagaaaga aggaaaaa                           1298


<210> SEQ ID NO 4
<211> LENGTH: 2236
<212> TYPE: DNA
<213> ORGANISM: Homo Sapiens

<400> SEQUENCE: 4

cctggcccgg tcgcggtcgc ggctctttcc agctcctggc agccgggcac ccgaaggaac     60

gggtcgtgca acgacgcagc tggacctggc ccagccatgg accgaaaagt ggcccgagaa    120

ttccggcata aggtggattt tctgattgaa aatgatgcag agaaggacta tctctatgat    180

gtgctgcgaa tgtaccacca gaccatggac gtggccgtgc tcgtgggaga cctgaagctg    240

gtcatcaatg aacccagccg tctgcctctg tttgatgcca ttcggccgct gatcccactg    300
```

-continued

```
aagcaccagg tggaatatga tcagctgacc ccccggcgct ccaggaagct gaaggaggtg    360

cgtctggacc gtctgcaccc cgaaggcctc ggcctgagtg tgcgtggtgg cctggagttt    420

ggctgtgggc tcttcatctc ccacctcatc aaaggcggtc aggcagacag cgtcgggctc    480

caggtagggg acgagatcgt ccggatcaat ggatattcca tctcctcctg tacccatgag    540

gaggtcatca acctcattcg aaccaagaaa actgtgtcca tcaaagtgag acacatcggc    600

ctgatccccg tgaaaagctc tcctgatgag cccctcactt ggcagtatgt ggatcagttt    660

gtgtcggaat ctgggggcgt gcgaggcagc ctgggctccc ctggaaatcg ggaaaacaag    720

gagaagaagg tcttcatcag cctggtaggc tcccgaggcc ttggctgcag catttccagc    780

ggccccatcc agaagcctgg catctttatc agccatgtga aacctggctc cctgtctgct    840

gaggtgggat tggagatagg ggaccagatt gtcgaagtca atggcgtcga cttctctaac    900

ctggatcaca aggaggctgt aaatgtgctg aaaaatagcc gcagcctgac catctccatt    960

gtagctgcag ctggccggga gctgttcatg acagaccggg agcggctggc agaggcgcgg   1020

cagcgtgagc tgcagcggca ggagcttctc atgcagaagc ggctggcgat ggagtccaac   1080

aagatcctcc aggagcagca ggagatggag cggcaaagga gaaaagaaat tgcccagaag   1140

gcagcagagg aaaatgagag ataccggaag gagatggaac agattgtaga ggaggaagag   1200

aagtttaaga agcaatggga agaagactgg ggctcaaagg aacagctact cttgcctaaa   1260

accatcactg ctgaggtaca cccagtaccc cttcgcaagc caaagtatga tcagggagtg   1320

gaacctgagc tcgagcccgc agatgacctg gatggaggca cggaggagca gggagagcag   1380

gatttccgga aatatgagga aggctttgac ccctactcta tgttcacccc agagcagatc   1440

atggggaagg atgtccggct cctacgcatc aagaaggagg gatccttaga cctggccctg   1500

gaaggcggtg tggactcccc cattgggaag gtggtcgttt ctgctgtgta tgagcgggga   1560

gctgctgagc ggcatggtgg cattgtgaaa ggggacgaga tcatggcaat caacggcaag   1620

attgtgacag actacaccct ggctgaggct gacgctgccc tgcagaaggc ctggaatcag   1680

ggcggggact ggatcgacct tgtggttgcc gtctgccccc caaaggagta tgacgatgag   1740

ctgaccttct tgctgaagtc caaaagggga aaccaaattc acgcgttagg aaacagtgag   1800

ctccggcccc acctcgtgaa cacaaagcct cggaccagcc ttgagagagg ccacatgaca   1860

cacaccagat ggcatccttg ggacctgaat ctatcaccca ggaatctcaa actccctttg   1920

gccctgaacc agggccagat aaggaacagc tcgggccact tttttgaagg ccaatgtgga   1980

ggaaagggag cagccagccg tttgggagaa gatctcaagg atccagactc tcattccttt   2040

cctctggccc agtgaatttg gtctctccca gctttggggg actccttcct tgaaccctaa   2100

taagacccca ctggagtctc tctctctcca tccctctcct ctgccctctg ctctaattgc   2160

tgccaggatt gtcactccaa accttactct gagctcatta ataaaataaa cagatttatt   2220

ttccagctta aaaaaa                                                   2236
```

```
<210> SEQ ID NO 5
<211> LENGTH: 2162
<212> TYPE: DNA
<213> ORGANISM: Homo Sapiens

<400> SEQUENCE: 5

cctggcccgg tcgcggtcgc ggctctttcc agctcctggc agccgggcac ccgaaggaac     60

gggtcgtgca acgacgcagc tggacctggc ccagccatgg accgaaaagt ggcccgagaa    120
```

-continued

```
ttccggcata aggtggattt tctgattgaa aatgatgcag agaaggacta tctctatgat    180
gtgctgcgaa tgtaccacca gaccatggac gtggccgtgc tcgtgggaga cctgaagctg    240
gtcatcaatg aacccagccg tctgcctctg tttgatgcca ttcggccgct gatcccactg    300
aagcaccagg tggaatatga tcagctgacc ccccggcgct ccaggaagct gaaggaggtg    360
cgtctggacc gtctgcaccc cgaaggcctc ggcctgagtg tgcgtggtgg cctggagttt    420
ggctgtgggc tcttcatctc ccacctcatc aaaggcggtc aggcagacag cgtcgggctc    480
caggtagggg acgagatcgt ccggatcaat ggatattcca tctcctcctg tacccatgag    540
gaggtcatca acctcattcg aaccaagaaa actgtgtcca tcaaagtgag acacatcggc    600
ctgatccccg tgaaaagctc tcctgatgag cccctcactt ggcagtatgt ggatcagttt    660
gtgtcggaat ctgggggcgt gcgaggcagc ctgggctccc ctggaaatcg ggaaaacaag    720
gagaagaagg tcttcatcag cctggtaggc tcccgaggcc ttggctgcag catttccagc    780
ggccccatcc agaagcctgg catctttatc agccatgtga aacctggctc cctgtctgct    840
gaggtgggat tggagatagg ggaccagatt gtcgaagtca atggcgtcga cttctctaac    900
ctggatcaca aggaggctgt aaatgtgctg aaaaatagcc gcagcctgac catctccatt    960
gtagctgcag ctggccggga gctgttcatg acagaccggg agcggctggc agaggcgcgg   1020
cagcgtgagc tgcagcggca ggagcttctc atgcagaagc ggctggcgat ggagtccaac   1080
aagatcctcc aggagcagca ggagatggag cggcaaagga gaaaagaaat tgcccagaag   1140
gcagcagagg aaaatgagag ataccggaag gagatggaac agattgtaga ggaggaagag   1200
aagtttaaga agcaatggga agaagactgg ggctcaaagg aacagctact cttgcctaaa   1260
accatcactg ctgaggtaca cccagtaccc cttcgcaagc caaagtgatt tccggaaata   1320
tgaggaaggc tttgacccct actctatgtt caccccagag cagatcatgg ggaaggatgt   1380
ccggctccta cgcatcaaga aggagggatc cttagacctg gccctggaag gcggtgtgga   1440
ctcccccatt gggaaggtgg tcgtttctgc tgtgtatgag cggggagctg ctgagcggca   1500
tggtggcatt gtgaaagggg acgagatcat ggcaatcaac ggcaagattg tgacagacta   1560
caccctggct gaggctgacg ctgccctgca gaaggcctgg aatcagggcg gggactggat   1620
cgaccttgtg gttgccgtct gcccccccaaa ggagtatgac gatgagctga ccttcttgct   1680
gaagtccaaa aggggaaacc aaattcacgc gttaggaaac agtgagctcc ggccccacct   1740
cgtgaacaca aagcctcgga ccagccttga gagaggccac atgacacaca ccagatggca   1800
tccttgggac ctgaatctat cacccaggaa tctcaaactc cctttggccc tgaaccaggg   1860
ccagataagg aacagctcgg gccacttttt tgaaggccaa tgtggaggaa agggagcagc   1920
cagccgtttg ggagaagatc tcaaggatcc agactctcat tcctttcctc tggcccagtg   1980
aatttggtct ctcccagctt tggggggactc cttccttgaa ccctaataag accccactgg   2040
agtctctctc tctccatccc tctcctctgc cctctgctct aattgctgcc aggattgtca   2100
ctccaaacct tactctgagc tcattaataa aataaacaga tttattttcc agcttaaaaa   2160
aa                                                                  2162
```

<210> SEQ ID NO 6
<211> LENGTH: 1789
<212> TYPE: DNA
<213> ORGANISM: Homo Sapiens

<400> SEQUENCE: 6

```
cttctggatg catccgagaa gctaaaactt acttatgagg aaaagtgtga aattgaggaa     60
```

-continued

```
tcccaattga agtttttgag gaacgactta gctgaatatc agagaacttg tgaagatctt    120

aaagagcaac taaagcataa agaatttctt ctggctgcta atacttgtaa ccgtgttggt    180

ggtctttgtt tgaaatgtgc tcagcatgaa gctgttcttt cccaaaccca tactaatgtt    240

catatgcaga ccatcgaaag actggttaaa gaaagagatg acttgatgtc tgcactagtt    300

tccgtaagga gcagcttggc agatacgcag caaagagaag caagtgctta tgaacaggtg    360

aaacaagttt tgcaaatatc tgaggaagcc aattttgaaa aaaccaaggc tttaatccag    420

tgtgaccagt tgaggaagga gctggagagg caggcggagc gacttgaaaa agaacttgca    480

tctcagcaag agaaaagggc cattgagaaa gacatgatga aaaaggaaat aacgaaagaa    540

agggagtaca tgggatcaaa gatgttgatc ttgtctcaga atattgccca actggaggcc    600

caggtggaaa aggttacaaa ggaaaagatt tcagctatta atcaactgga ggaaattcaa    660

agccagctgg cttctcggga aatggatgtc acaaaggtgt gtggagaaat gcgctatcag    720

ctgaataaaa ccaacatgga gaaggatgag gcagaaaagg agcacagaga gttcagagca    780

aaaactaaca gggatcttga aattaaagat caggaaatag agaaattgag aatagaactg    840

gatgaaagca aacaacactt ggaacaggag cagcagaagg cagccctggc cagagaggag    900

tgcctgagac taacagaact gctgggcgaa tctgagcacc aactgcacct caccagacag    960

gaaaaagata gcattcagca gagctttagc aaggaagcaa aggcccaagc ccttcaggcc   1020

cagcaaagag agcaggagct gacacagaag atacagcaaa tggaagccca gcatgacaaa   1080

actgaaaatg aacagtattt gttgctgacc tcccagaata catttttgac aaagttaaag   1140

gaagaatgct gtacattagc caagaaactg gaacaaatct ctcaaaaaac cagatctgaa   1200

atagctcaac tcagtcaaga aaaaaggtat acatatgata aattgggaaa gttacagaga   1260

agaaatgaag aattggagga acagtgtgtc cagcatggga gagtacatga gacgatgaag   1320

caaaggctaa ggcagctgga taagcacagc caggccacag cccagcagct ggtgcagctc   1380

ctcagcaagc agaaccagct tctcctggag aggcagagcc tgtcggaaga ggtggaccgg   1440

ctgcggaccc agttacccag catgccacaa tctgattgct gacctggatg gaacagagtg   1500

aaataaatga attacaaaga gatatttaca ttcatctggt ttagacttaa tatgccacaa   1560

cgcaccacga ccttcccagg gtgacaccgc ctcagcctgc agtggggctg gtcctcatca   1620

acgcgggcgc tgtccccgca cgcagtcggg ctggagctgg agtctgactc tagctgagca   1680

gactcctggt gtatgttttc agaaatggct tgaagttatg tgtttaaatc tgctcattcg   1740

tatgctaggt tatacatatg attttcaata aatgaacttt ttaaagaaa               1789
```

<210> SEQ ID NO 7
<211> LENGTH: 1306
<212> TYPE: DNA
<213> ORGANISM: Homo Sapiens

<400> SEQUENCE: 7

```
aaaaatagcc gcagcctgac catctccatt gtagctgcag ctggccggga gctgttcatg     60

acagaccggg agcggctggc agaggcgcgg cagcgtgagc tgcagcggca ggagcttctc    120

atgcagaagc ggctggcgat ggagtccaac aagatcctcc aggagcagca ggagatggag    180

cggcaaagga gaaaagaaat tgcccagaag gcagcagagg aaaatgagag ataccggaag    240

gagatggaac agattgtaga ggaggaagag aagtttaaga agcaatggga agaagactgg    300

ggctcaaagg aacagctact cttgcctaaa accatcactg ctgaggtaca cccagtaccc    360
```

-continued

```
cttcgcaagc caaagtatga tcagggagtg gaacctgagc tcgagcccgc agatgacctg    420

gatggaggca cggaggagca gggagagcag gatttccgga aatatgagga aggctttgac    480

ccctactcta tgttcacccc agagcagatc atggggaagg atgtccggct cctacgcatc    540

aagaaggagg gatccttaga cctggccctg gaaggcggtg tggactcccc cattgggaag    600

gtggtcgttt ctgctgtgta tgagcgggga gctgctgagc ggcatggtgg cattgtgaaa    660

ggggacgaga tcatggcaat caacggcaag attgtgacag actacaccct ggctgaggct    720

gacgctgccc tgcagaaggc ctggaatcag ggcggggact ggatcgacct tgtggttgcc    780

gtctgccccc caaaggagta tgacgatgag ctgaccttct tgctgaagtc caaaagggga    840

aaccaaattc acgcgttagg aaacagtgag ctccggcccc acctcgtgaa cacaaagcct    900

cggaccagcc ttgagagagg ccacatgaca cacaccagat ggcatccttg ggacctgaat    960

ctatcaccca ggaatctcaa actccctttg gccctgaacc agggccagat aaggaacagc   1020

tcgggccact tttttgaagg ccaatgtgga ggaaagggag cagccagccg tttgggagaa   1080

gatctcaagg atccagactc tcattccttt cctctggccc agtgaatttg gtctctccca   1140

gctttggggg actccttcct tgaaccctaa taagacccca ctggagtctc tctctctcca   1200

tccctctcct ctgccctctg ctctaattgc tgccaggatt gtcactccaa accttactct   1260

gagctcatta ataaaataaa cagatttatt ttccagctta aaaaaa                  1306
```

```
<210> SEQ ID NO 8
<211> LENGTH: 2289
<212> TYPE: DNA
<213> ORGANISM: Homo Sapiens

<400> SEQUENCE: 8

cctggcccgg tcgcggtcgc ggctctttcc agctcctggc agccgggcac ccgaaggaac     60

gggtcgtgca acgacgcagc tggacctggc ccagccatgg accgaaaagt ggcccgagaa    120

ttccggcata aggtggattt tctgattgaa aatgatgcag agaaggacta tctctatgat    180

gtgctgcgaa tgtaccacca gaccatggac gtggccgtgc tcgtgggaga cctgaagctg    240

gtcatcaatg aacccagccg tctgcctctg tttgatgcca ttcggccgct gatcccactg    300

aagcaccagg tggaatatga tcagctgacc ccccggcgct ccaggaagct gaaggaggtg    360

cgtctggacc gtctgcaccc cgaaggcctc ggcctgagtg tgcgtggtgg cctggagttt    420

ggctgtgggc tcttcatctc ccacctcatc aaaggcggtc aggcagacag cgtcgggctc    480

caggtagggg acgagatcgt ccggatcaat ggatattcca tctcctcctg tacccatgag    540

gaggtcatca acctcattcg aaccaagaaa actgtgtcca tcaaagtgag acacatcggc    600

ctgatccccg tgaaaagctc tcctgatgag cccctcactt ggcagtatgt ggatcagttt    660

gtgtcggaat ctgggggcgt gcgaggcagc ctgggctccc ctggaaatcg ggaaaacaag    720

gagaagaagg tcttcatcag cctggtaggc tcccgaggcc ttggctgcag catttccagc    780

ggccccatcc agaagcctgg catctttatc agccatgtga aacctggctc cctgtctgct    840

gaggtgggat tggagatagg ggaccagatt gtcgaagtca atggcgtcga cttctctaac    900

ctggatcaca aggaggctgt aaatgtgctg aaaaatagcc gcagcctgac catctccatt    960

gtagctgcag ctggccggga gctgttcatg acagaccggg agcggctggc agaggcgcgg   1020

cagcgtgagc tgcagcggca ggagcttctc atgcagaagc ggctggcgat ggagtccaac   1080

aagatcctcc aggagcagca ggagatggag cggcaaagga gaaaagaaat tgcccagaag   1140

gcagcagagg aaaatgagag ataccggaag gagatggaac agattgtaga ggaggaagag   1200
```

-continued

```
aagtttaaga agcaatggga agaagactgg ggctcaaagg aacagctact cttgcctaaa   1260
accatcactg ctgaggtaca cccagtaccc cttcgcaagc caaagtatga tcagggagtg   1320
gaacctgagc tcgagcccgc agatgacctg gatggaggca cggaggagca gggagagcag   1380
ccacaggaga tgttgaagag gatggtggtt tatcaagaca gcattcaaga caagatttcc   1440
ggaaatatga ggaaggcttt gacccctact ctatgttcac cccagagcag atcatgggga   1500
aggatgtccg gctcctacgc atcaagaagg agggatcctt agacctggcc ctggaaggcg   1560
gtgtggactc ccccattggg aaggtggtcg tttctgctgt gtatgagcgg ggagctgctg   1620
agcggcatgg tggcattgtg aaaggggacg agatcatggc aatcaacggc aagattgtga   1680
cagactacac cctggctgag gctgacgctg ccctgcagaa ggcctggaat cagggcgggg   1740
actggatcga ccttgtggtt gccgtctgcc ccccaaagga gtatgacgat gagctgacct   1800
tcttgctgaa gtccaaaagg ggaaaccaaa ttcacgcgtt aggaaacagt gagctccggc   1860
cccacctcgt gaacacaaag cctcggacca gccttgagag aggccacatg acacacacca   1920
gatggcatcc ttgggacctg aatctatcac ccaggaatct caaactccct ttggccctga   1980
accagggcca gataaggaac agctcgggcc actttttga aggccaatgt ggaggaaagg   2040
gagcagccag ccgtttggga gaagatctca aggatccaga ctctcattcc tttcctctgg   2100
cccagtgaat ttggtctctc ccagctttgg gggactcctt ccttgaaccc taataagacc   2160
ccactggagt ctctctctct ccatccctct cctctgccct ctgctctaat tgctgccagg   2220
attgtcactc caaaccttac tctgagctca ttaataaaat aaacagattt attttccagc   2280
ttaaaaaaa                                                           2289
```

ISOLATED NUCLEIC ACID MOLECULES ASSOCIATED WITH COLON CANCER AND METHODS FOR DIAGNOSING AND TREATING COLON CANCER

RELATED APPLICATIONS

This application is a divisional of U.S. application Ser. No. 08/948,705, filed on Oct. 10, 1997, now issued as U.S. Pat. No. 6,043,084.

FIELD OF THE INVENTION

1. Background and Prior Art

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines. Transfectants are screened for the expression of tumor antigens via their ability to provoke reactions by anti-tumor cytolytic T cell clones. The biochemical approach, exemplified by, e.g., Mandelboim, et al., Nature 369: 69 (1994) incorporated by reference, is based on acidic elution of peptides which have bound to MHC-class I molecules of tumor cells, followed by reversed-phase high performance liquid chromography (HPLC). Antigenic peptides are identified after they bind to empty MHC-class I molecules of mutant cell lines, defective in antigen processing, and induce specific reactions with cytolytic T-lymphocytes ("CTLs"). These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; second, they depend on the establishment of CTLs with predefined specificity; and third, their relevance in vivo for the course of the pathology of disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. Pat. Nos. 5,698,396 and 6,025,191. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patents and Sahin, et al., supra, as well as Crew, et al., EMBO J. 144: 2333–2340 (1995).

The SEREX methodology has now been applied to colon cancer samples. Several nucleic acid molecules have been newly isolated and sequenced, and are now associated with stomach cancer. Further, a pattern of expression involving these, as well as previously isolated genes has been found to be associated with colon cancer. These results are the subject of this application, which is elaborated upon in the disclosure which follows.

DETAILED DESCRIPTION OF PREFERRED EMBODIMENTS

Example 1

Tumor samples were obtained as surgical samples, and were frozen at −80° C. until ready for use.

Total RNA was then isolated from the samples, using the well known guanidium thiocyanate method of Chirgwin, et al., Biochemistry 18: 5294–5299 (1979), incorporated by reference. The thus obtained total RNA was then purified to isolate all poly A+ RNA, using commercially available products designed for this purpose.

The poly $A^+$ RNA was then converted into cDNA, and ligated into λZAP, a well known expression vector.

Three cDNA libraries were constructed in this way, using colorectal carcinoma samples. A fourth library, also from colorectal carcinoma, was prepared, albeit in a different way. The reasons for this difference will be clear in the examples, infra.

The fourth library was an IgG subtraction library, prepared by using a subtraction partner, generated by PCR amplification of a cDNA clone which encoded an IgG molecule. See, e.g., Ace et al, Endocrinology 134: 1305–1309 (1994), and incorporated by reference in its entirety.

This is done to eliminate any false, positive signals resulting from interaction of cDNA clones which encode IgG, with the anti-human IgG used in the assay, as described infra. PCR product was biotinylated, and hybridized with denatured second strand cDNA, at 68° C. for 18 hours. Biotinylated hybrid molecules were coupled to streptavidin, and then removed by phenol chloroform extraction. Any remaining cDNA was also ligated into λZAP. All libraries were amplified, prior to immunoscreening discussed infra.

Example 2

Immunoscreening was carried out, using sera obtained from patients undergoing routine diagnostic and therapeutic procedures. The sera were stored at −70° C. prior to use. Upon thawing, the sera were diluted at 1:10 in Tris buffered saline (pH 7.5), and were then passed through Sepharose 4B columns. First, the sera were passed through columns which had *E. coli* Y1090 lysates coupled thereto, and then lysates from bacteriophage infected *E. coli* BNN97 lysates. Final serum dilutions were then prepared in 0.2% non-fat dried milk/Tris buffered saline.

The method of Sahin et al., Proc. Natl. Acad. Sci. USA 92: 11810–11813 (1995), and, U.S. Pat. No. 5,698,396, both of which are incorporated by reference, was used, with some modifications. Specifically recombinant phage at a concentration of $4\times10^3$ phages per 15 cm plate (pfus), were amplified for six hours, after which they were transferred to nitrocellulose membranes for 15 hours. Then, the membranes were blocked with 5% nonfat dried milk.

As an alternative to the IgG subtraction, discussed supra, membranes were prescreened in a 1:2000 dilution of peroxidase conjugated, Fc fragment specific goat anti-human IgG, for one hour, at room temperature. Color was developed using 3,3-diaminobenzidine tetrahydrochloride, which permitted scoring of IgG encoding clones.

Membranes were then incubated in 1:100 dilutions of autologous sera, which had been pretreated with the Sepharose 4B columns, as described supra. The filters were then incubated, in a 1:3000 dilution of alkaline phosphatase conjugated Fc fragment specific, goat anti-human IgG, for one hour, at room temperature. The indicator system 4-nitroblue tetrazolium chloride/5-bromo-4-chloro-3-indolylphosphate was then added, and color development assessed. Any positive clones were subcloned, and retested, except the tine on the nitrocellulose membrane was reduced to three hours. A total of forty-eight positive clones were identified.

Analysis of probes for SEQ ID NOS: 1 and 2 confirmed their universal expression.

Example 3

Example 2 described work using autologous serum. The positive clones were then rescreened, using allogeneic serum, following the same method discussed supra, in example 2, except IgG prescreening was omitted. The allogeneic sera was obtained from sixteen normal blood donors, and twenty nine patients who had been diagnosed with colorectal cancer.

The analysis with the two types of serum revealed that fourteen reacted with a subset of sera from normal and cancer patients, twenty-eight only with autologous sera, and six with both allogeneic and autologous sera. Over 60% of the allogeneic serum samples tested reacted with at least one of these positive clones. About 20% reacted with two or more.

Example 4

In view of the results described in example 3, further experiments were carried out using serum samples from patients with other forms of cancer, i.e., renal cancer (13 samples), lung cancer (23 samples), and breast cancer (10 samples). The results are set forth in Table I which follow:

| Clone Number | Normal Sera | Colon Cancer | Renal Cancer | Lung Cancer | Breast Cancer |
|---|---|---|---|---|---|
| NY-Co-8 | 0/16 | 8/29 | 1/13 | 0/23 | 0/10 |
| NY-Co-9 | 0/16 | 5/29 | 1/13 | 1/23 | 0/10 |
| NY-Co-13 | 0/16 | 5/29 | 0/13 | 0/23 | 0/10 |
| NY-Co-16 | 0/16 | 3/29 | 0/13 | 0/23 | 0/10 |
| NY-Co-20 | 0/16 | 4/29 | 0/13 | 0/23 | 0/10 |
| NY-Co-38 | 0/16 | 4/29 | 3/13 | 0/23 | 1/10 |

Example 5

Following the screening work described supra, the cDNA inserts were purified and sequenced, following standard methods.

Of the six clones which were identified as being reactive with autologous and allogeneic cancer serum, and not with normal serum, two were found to be identical to previously identified molecules. Four others were found to have little or no homology to known sequences. These are presented as SEQ ID NOS: 1–4. Of twenty seven allogeneic colon cancer serum samples tested, 67% reacted with at least one of these antigens.

Example 6

The expression pattern of mRNA corresponding to SEQ ID NOS: 1, 2 and 4, as well as other sequences identified via the preceding examples was determined. To do this, RT-PCR was carried out on a panel of RNA samples, taken from normal tissue. The panel contained RNA of lung, testis, small intestine, colon, breast, liver and placenta tissues. The RNA was purchased from a commercial source. RNA from a colon tumor sample was also included. All samples were set up for duplicate runs, so that genomic DNA contamination could be accounted for. In the controls, no reverse transcriptase was used.

Primers were designed which were specific for the cDNA, which would amplify 5'-fragments, from 300 to 400 base pairs in length. The PCR reactions were undertaken at an annealing temperature of 68° C. Where appropriate, 5' and 3'-RACE reactions were undertaken, using gene specific primers, and adapter primers, together with commercially available reagents. Specifically, SEQ ID NOS: 2 and 4 were tested using RACE. The resulting products were subcloned into vector pCR 2.1, screened via PCR using internal primers, and then sequenced.

SEQ ID NOS: 1 and 2 were found to be amplified in all tissues tested. SEQ ID NO: 4 was found in colon tumor, colon metastasis, gastric cancer, renal cancer and colon cancer cell lines Colo 204 and HT29, as well as in normal colon, small intestine, brain, stomach, testis, pancreas, liver, lung, heart, fetal brain, mammary gland, bladder, adrenal gland tissues. It is was not found in normal uterine, skeletal muscle, peripheral blood lymphocytes, placental, spleen thymus, or esophagus tissue, nor in lung cancer.

The analysis also identified differential expression of a splice variant of SEQ ID NO: 4, i.e., SEQ ID NO: 5. When the two sequences were compared, it was found that SEQ ID NO: 4 encodes a putative protein of 652 amino acids, and molecular weight of 73,337 daltons. SEQ ID NO: 5, in contrast, lacks an internal 74 base pairs, corresponding to nucleotides 1307–1380 of SEQ ID NO: 4. The deletion results in formation of a stop codon at the splice function, and a putative protein of 404 amino acids, and molecular weight 45,839. The missing segment results in the putative protein lacking a PEST protein degradation sequence, thereby suggesting a longer half life for this protein.

In additional experiments, primers designed not to differentiate between SEQ ID NOS: 4 and 5 resulted in almost universal amplification (placenta being the only exception). In contrast, when primers specific for SEQ ID NO: 5 were used differences were seen in normal pancreatic, liver, lung, heart, fetal brain, mammary gland, bladder, and adrenal gland tissue, where there was no expression of SEQ ID NO: 5 found.

Example 7

Northern blotting was also carried out for SEQ ID NOS: 1, 2, 4 and 5. To do this, the same commercially available RNA libraries discussed supra were used.

Samples (2 ug) of polyA$^+$ RNA were analyzed from these samples, using random, $^{32}$P labelled probes 300–360 nucleotides in length, obtained from PCR products. These probes were hybridized to the RNA, for 1.5 hours, at 68° C., followed by two washes at 0.1×SSC, 0.1% SDS, 68° C., for 30 minutes each time.

SEQ ID NOS: 1 and 2 were again found to be universally expressed.

Example 8

Further screening identified additional isoforms of SEQ ID NOS: 1 and 4. These are set forth as SEQ ID NOS: 6, 7 and 8. The isoform represented by SEQ ID NO: 6 is a naturally occurring splice variant of SEQ ID NO: 1, found in normal colon. SEQ ID NO: 7, which is an isoform of SEQ ID NO: 4, was found in brain tissue, primarily spinal chord and medulla. SEQ ID NO: 8, was found in normal kidney and in colon tumors, metastasized colon cancer, gastric cancer, and in colon cancer cell line Colo 205. It was not found in any normal tissue other than kidney.

The foregoing examples demonstrate several features of the invention. These include diagnostic methods for determining presence of transformed cells, such as colon cancer cells, in a sample. The sample may contain whole cells or it may be, e.g., a body fluid sample, or an effusion, etc., where the sample may contain cells, but generally will contain shed antigen. The experiments indicate that there is a family of proteins, expression of which is associated with colon cancer. Hence, the invention involves, inter alia, detecting at least two of the proteins encoded by any of SEQ ID NOS: 1–5, wherein presence of these is indicative of a pathology, such as colon cancer or other type of related condition. Exemplary of the type of diagnostic assays which can be carried out are immunoassays, amplification assays (e.g., PCR), or, what will be referred to herein as a "display array". "Display array" as used herein refers to a depiction of the protein profile of a given sample. Exemplary of such displays are 2-dimensional electrophoresis, banding patterns such as SDS-gels, and so forth. Thus, one aspect of the invention involves diagnosing colon cancer or a related condition by determining protein display of a sample, wherein a determination of at least one of the proteins, or expression of their genes, is indicative of colon cancer or a related condition. There are many ways to carry out these assays. For example, as indicated herein, antibodies to the proteins were found in patient samples. One can assay for these antibodies using, e.g., the methodology described herein, or by using a purified protein or proteins or antigenic fragment thereof, and so forth. One can also assay for the protein itself, using antibodies, which may be isolated from samples, or generated using the protein and standard techniques. This antibodies can then be labelled, if desired, and used in standard immunoassays. These antibodies or oligonucleotide probes/primers may also be used to examine biopsied tissue samples, e.g., to diagnose precancerous conditions, early stage cancers, and so forth.

Similarly, any and all nucleic acid hybridization systems can be used, including amplification assays, such as PCR, basic probe hybridization assays, and so forth. The antibodies, such as polyclonal antibodies, monoclonal antibodies, the hybridomas which produce them, recombinantly produced antibodies, binding fragments of these, hybridization kits, DNA probes, and so forth, are all additional features of the invention.

Any of these assays can also be used in progression/regression studies. One can monitor the course of an abnormality such as colon cancer which involve expression of any one of the proteins, the expression of which is governed by the nucleic acid molecules SEQ ID NOS: 1–5, simply by monitoring levels of the protein, its expression, and so forth using any or all of the methods set forth supra.

As has been indicated supra, the isolated nucleic acid molecules which comprise the nucleotide sequences set forth in SEQ ID NOS: 1–5 are new, in that they have never been isolated before. These nucleic acid molecules may be used as a source to generate colon cancer specific proteins and peptides derived therefrom, and oligonucleotide probes which can themselves be used to detect expression of these genes. Hence, a further aspect of the invention is an isolated nucleic acid molecule which comprises any of the nucleotide sequences set forth in SEQ ID NOS: 1–5, or molecules whose complements hybridize to one or more of these nucleotide sequences, under stringent conditions, expression vectors comprising these molecules, operatively linked to promoters, cell lines and strains transformed or transfected with these, and so forth. "Stringent conditions", is used herein, refers to condition such as those specified in U.S. Pat. No. 5,342,774, i.e., 18 hours of hybridization at 65° C., followed by four one hour washes at 2×SSC, 0.1% SDS, and a final wash at 0.2×SSC, more preferably 0.1×SSC, 0.1% SDS for 30 minutes, as well as alternate conditions which afford the same level of stringency, and more stringent conditions.

It should be clear that these methodologies may also be used to track the efficacy of a therapeutic regime. Essentially, one can take a baseline value for the protein or proteins being tested, using any of the assays discussed supra, administer a given therapeutic, and then monitor levels of the protein or proteins thereafter, observing changes in protein levels as indicia of the efficacy of the regime.

The identification of the proteins and nucleic acid molecules set forth herein as being implicated in pathological conditions such as colon cancer also suggests a number of therapeutic approaches to such conditions. The experiments set forth supra establish that antibodies are produced in response to expression of these proteins, suggesting their use as a vaccine. Hence, a further embodiment of the invention is the treatment of conditions which are characterized by expression of one or more of the subject proteins, via immunotherapeutic approaches. One of these approaches is the administration of an amount of one or more these proteins, or an immunogenic peptide derived therefrom in an amount sufficient to provoke or augment an immune response. The proteins or peptides may be combined with one or more of the known immune adjuvants, such as saponins GM-CSF interleukins, and so forth. If the peptides are too small to generate a sufficient antibody response, they can be coupled to the well known conjugates used to stimulate responses.

Similarly, the immunotherapeutic approaches include administering an amount of inhibiting antibodies sufficient to inhibit the protein or proteins. These antibodies may be, e.g., antibodies produced via any of the standard approaches elaborated upon supra.

T cell responses may also be elicited by using peptides derived from the proteins which then complex, non-covalently, with MHC molecules, thereby stimulating proliferation of cytolytic T cells against any such complexes in the subject. It is to be noted that the T cells may also be elicited in vitro, and then reperfused into the subject being treated.

Note that the generation of T cells and/or antibodies can also be accomplished by administering cells, preferably treated to be rendered non-proliferative, which present relevant T cell or B cell epitopes for response.

The therapeutic approaches may also include gene therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the well known BCG vaccine, and so forth.

An additional DNA based therapeutic approach is the use of a vector which comprises one or more nucleotide sequences, preferably a plurality of these, each of which encodes an immunoreactive peptide derived from the expressed proteins. One can combine these peptides expressing sequences in all possible variations, such as one from each protein, several from one or more protein and one from each of the additional proteins, a plurality from some and none from others, and so forth.

Other features of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated protein encoded by an isolated nucleic acid molecule selected from the group consisting of: SEQ ID NOs: 1, 2, 3, 4 and 5.

2. A composition of matter comprising a protein encoded by a nucleic acid molecule selected from the group consisting of SEQ ID NO: 1, 2, 3, 4 and 5.

3. The composition of matter of claim 2, further comprising an adjuvant.

4. The composition of matter of claim 3, wherein said adjuvant is a saponin, GM-CSF, or an interleukin.

5. The isolated protein of claim 1, wherein the isolated nucleic acid molecule consists of SEQ ID NO:1.

6. The isolated protein of claim 1, wherein the isolated nucleic acid molecule consists of SEQ ID NO:2.

7. The isolated protein of claim 1, wherein the isolated nucleic acid molecule consists of SEQ ID NO:3.

8. The isolated protein of claim 1, wherein the isolated nucleic acid molecule consists of SEQ ID NO:4.

9. The isolated protein of claim 1, wherein the isolated nucleic acid molecule consists of SEQ ID NO:5.

10. The composition of matter of claim 2, wherein the nucleic acid molecule consists of the nucleotide sequence set forth in SEQ ID NO: 1.

11. The composition of matter of claim 2, wherein the nucleic acid molecule consists of the nucleotide sequence set forth in SEQ ID NO:2.

12. The composition of matter of claim 2, wherein the at least one nucleic acid molecule consists of the nucleotide sequence set forth in SEQ ID NO:3.

13. The composition of matter of claim 2, wherein the nucleic acid molecule consists of the nucleotide sequence set forth in SEQ ID NO:4.

14. The composition of matter of claim 2, wherein the nucleic acid molecule consists of the nucleotide sequence set forth in SEQ ID NO:5.

* * * * *

UNITED STATES PATENT AND TRADEMARK OFFICE

CERTIFICATE OF CORRECTION

PATENT NO. : 6,982,316 B1
APPLICATION NO. : 09/502945
DATED : January 3, 2006
INVENTOR(S) : Matthew J. Scanlan et al.

It is certified that error appears in the above-identified patent and that said Letters Patent is hereby corrected as shown below:

Title page,
Item [57], ABSTRACT,
Line 2, should read -- are disclosed. The invention also discloses a diagnostic and --.

Column 24,
Lines 44-45, should read:
-- The composition of matter of claim 2, wherein the nucleic acid molecule consists of the nucleotide --.

Signed and Sealed this

Twenty-seventh Day of June, 2006

JON W. DUDAS
*Director of the United States Patent and Trademark Office*